United States Patent [19]
Silvian

[11] Patent Number: 4,742,831
[45] Date of Patent: May 10, 1988

[54] SELECTION AND ISOLATION APPARATUS FOR USE WITH ECG DEVICE

[75] Inventor: Sergiu Silvian, Pasadena, Calif.

[73] Assignee: Siemens-Pacesetter, Inc., Sylmar, Calif.

[21] Appl. No.: 800,478

[22] Filed: Nov. 21, 1985

[51] Int. Cl.$^4$ .............................................. A61B 5/04
[52] U.S. Cl. .................................... 128/710; 128/696; 128/902; 128/908
[58] Field of Search ............... 128/695, 696, 710, 902, 128/908

[56] References Cited

U.S. PATENT DOCUMENTS

| | | | |
|---|---|---|---|
| 3,690,313 | 9/1972 | Weppner et al. | 128/902 |
| 3,880,146 | 4/1975 | Everett et al. | 128/710 |
| 3,910,257 | 10/1975 | Fletcher et al. | 128/908 |
| 3,922,686 | 11/1975 | France et al. | 128/696 |
| 4,037,586 | 7/1977 | Grichnik | 128/731 |
| 4,106,494 | 8/1978 | McEachern | 128/419 D |
| 4,245,649 | 1/1981 | Schmidt-Anderson | 128/696 |
| 4,245,650 | 1/1981 | Welker et al. | 128/908 |

OTHER PUBLICATIONS

"Analog Dialog", vol. 5, No. 2, Feb.-Mar. '71, pp 10-11.
Markus, Modern Electronic Circuits Reference Manual, p. 532, "Heart Monitor" (McGraw-Hill, 1980).
Olschewski, "Unique Transformer Design Shrinks Hybrid Isolation Amplifier'3 s Size and Cost", *Electronics*, Jul. 20, 1978, pp. 105–112.

*Primary Examiner*—William E. Kamm
*Attorney, Agent, or Firm*—Bryant R. Gold

[57] ABSTRACT

Isolation circuitry for use with diagnostic ECG devices provides high common mode rejection and low leakage current using optoisolators in conjunction with an isolating operational amplifier. A predetermined pattern of binary input signals selectively energizes, via the optoisolators, a plurality of switches interposed between electrodes positioned on a patient's skin and the isolating operational amplifier. This selection couples a predetermined combination of electrodes to the isolating operational amplifier to provide the desired ECG output. The output from the isolating operational amplifier may be coupled directly to a recording device or coupled to a circuit which processes the ECG signal before the signal is recorded.

6 Claims, 3 Drawing Sheets

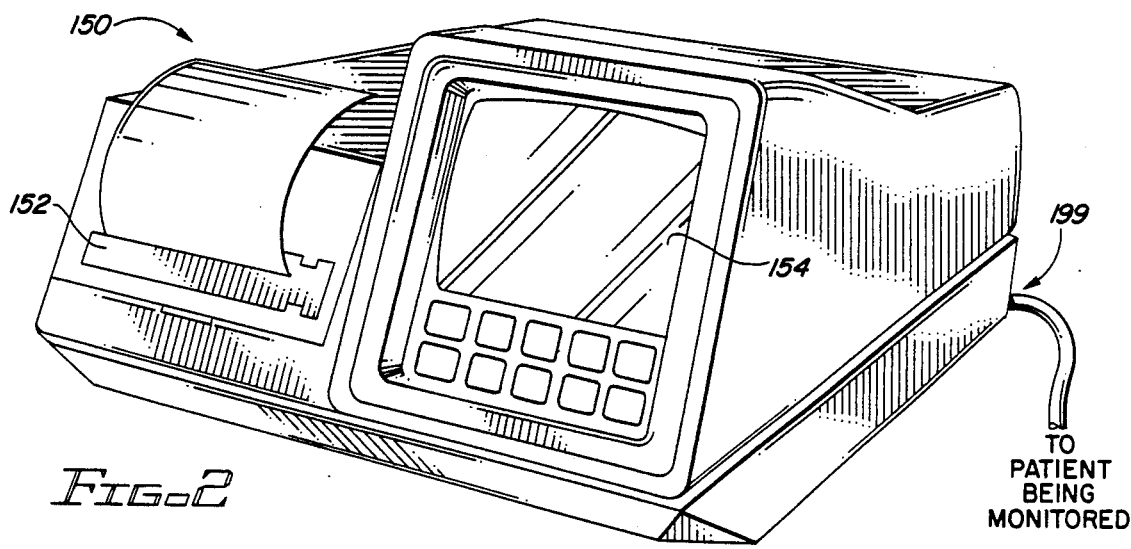
Fig. 2
| EXT. CONTROL | | | | SWITCH CONTROL | | | | | | | | |
|---|---|---|---|---|---|---|---|---|---|---|---|---|
| DEC. | $I_2$ | $I_1$ | $I_0$ | LEAD | a | b | c | d | e | f | g | −INPUT | +INPUT |
| 7 | 1 | 1 | 1 | — | | | | | | | | — | — |
| 6 | 1 | 1 | 0 | V | X | | | | X | X | X | $\dfrac{RA+LA+LL}{3}$ | C |
| 5 | 1 | 0 | 1 | aVF | | | | X | X | X | | $\dfrac{RA+LA}{2}$ | LL |
| 4 | 1 | 0 | 0 | aVL | | X | | | | X | X | $\dfrac{RA+LL}{2}$ | LA |
| 3 | 0 | 1 | 1 | aVR | | | X | | X | | X | $\dfrac{LA+LL}{2}$ | RA |
| 2 | 0 | 1 | 0 | III | | | | X | X | | | LA | LL |
| 1 | 0 | 0 | 1 | II | | | | X | | X | | RA | LL |
| 0 | 0 | 0 | 0 | I | | X | | | | X | | RA | LA |
X = SWITCH ON (CLOSED)
Fig. 4
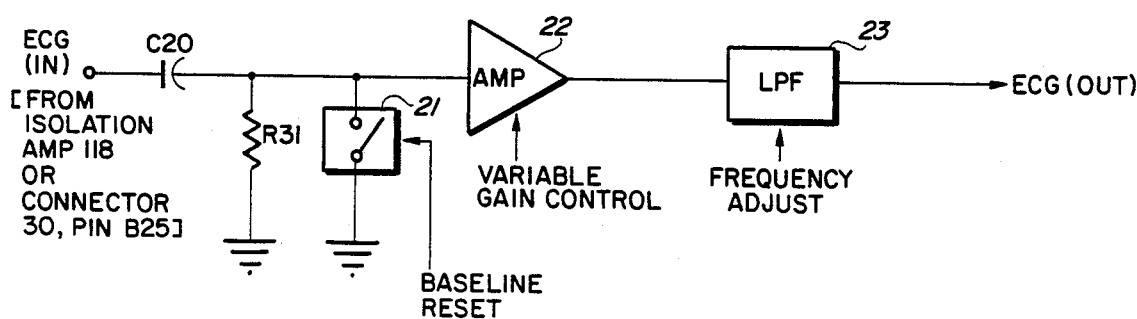
Fig. 5

SELECTION AND ISOLATION APPARATUS FOR USE WITH ECG DEVICE

BACKGROUND OF THE INVENTION

The present invention relates to ECG devices, and in particular to an ECG circuit which utilizes optoisolators in combination with an isolation operational amplifier to provide a safe, simple, reliable, and efficient means of extracting ECG signal information.

Electrocardiography (ECG) is the recording and examination of electrical signals which accompany the contraction of the heart or other muscle. Electrocardiograph electrodes are attached at desired locations on the body and the electrical activity generated by contraction of the heart muscle, as measured on the electrode leads, is connected to and recorded on an electrocardiograph in a conventional manner. However, because the signals thus generated are typically at low voltage levels, amplifier circuits coupled to the electrodes are needed in order to prevent masking of the signals by other extraneous electrical signals (noise). One technique known in the art for providing this amplifying function is to use a differential amplifier. A differential amplifier measures and amplifies only the difference between two input signals. Thus, if a common background signal is present in both input signals, the background signal will not be amplified because it is not part of the difference between the two input signals, but rather represents a common signal to both input signals. The rejection (non-amplification) of such a common signal is referred to in the art as common mode rejection. For ECG applications, the two inputs of a differential amplifier are respectively connected to the selected two points between which the ECG potential difference is to be measured. The differential amplifier advantegously amplifies this ECG potential difference to a much greater degree than other common mode signals that may be present, such as the 60 Hz power line signals that are commonly induced in the body. Another technique used for reducing the effect of external noise signals on the measured heart signal is to use shielded leads. That is, the signal leads connected to the electrodes are surrounded by a metallic screen or foil that is connected to ground or other fixed potential. This latter shielding technique is also utilized in the circuit of the present invention, but with the shield actively driven as will be shown.

Although these efforts to discriminate between the desired electrical voltage signal generated by the heart muscle and the electrical effects of the environment have generally been satisfactory, it is sometimes desirable to provide further discrimination between the sensed electrical signals. For example, modern ECG devices typically utilize multiple transformers on each electrode lead in conjunction with an applied carrier frequency in order to achieve a high common mode rejection and a high isolation factor. Over-voltage discharge elements are also utilized to protect the circuitry against high voltages, which high voltages may be present in the event a defibrillator device is used on the patient. A high isolation factor, which prevents currents from flowing from one part of the circuit to another where current is not intended to flow, is necessary to both protect the patient if the patient inadvertently is connected to ground or a high potential, such as a power line (thus forming a closed circuit loop), and in order to achieve an improved high common mode rejection of extraneous signals, such as the 60 Hz power line signal, thereby allowing the ECG signal to be more cleanly amplified and recorded or displayed.

Although the use of transformers on each patient lead provides a circuit having high common mode rejection and a high isolation factor, the transformers are expensive, bulky, and tend to be unreliable. Accordingly, what is needed is to provide an improved circuit for use with ECG devices that provides high common mode rejection, a high isolation factor (has low leakage current), and that is reliable, compact and relatively inexpensive. It is further desired that this circuit have the capability of sustaining without damage large voltage surges such as might occur if the patient requires defibrillation during recording of the ECG signal. Moreover where multiple electrode leads are placed on the patient, it is desirable to be able to selectively connect the ECG device between selected electrodes or combinations of electrodes.

SUMMARY OF THE INVENTION

The present invention provides a switching electrical isolation circuit for use with multiple electrode ECG recording devices that provides high common mode rejection and low leakage current. The isolation circuit of the present invention utilizes optical isolators in conjunction with an isolation operational amplifier. A predetermined pattern of binary input signals selectively energizes, through the optical isolators, a plurality of switches interposed between the electrodes positioned on a patient and the operational amplifier in order to connect a predetermined combination of the electrodes to the inputs of the operational amplifier. The isolated output from the operational amplifier is encoupled either directly to a recording device or coupled to a circuit which processes the ECG signal before the signal is recorded or displayed. The isolation circuit of the present invention further includes means for protecting the circuitry and the recording device from high voltages which may have to be applied to the patient in an attempt to correct a malfunctioning heart.

Advantageously, the present invention is realized using relatively inexpensive, reliable components that are configured in an isolated circuit that provides reliable, safe operation. The patient is completely isolated from the ECG recording device, its associated power supplies, and the electrode selection control means. The high common mode rejection and low leakage current of the isolation circuit advantageously allows an accurate ECG recording to be taken without subjecting the patient to any possible electrical hazards or other dangers.

BRIEF DESCRIPTION OF THE DRAWINGS

For a better understanding of the invention, as well as a better explanation of the further features and objects thereof, reference is made to the following description which is to be read in conjunction with the accompanying drawings wherein:

FIG. 2 is a perspective view of a pacer programming device within which the present invention may be housed in accordance with a preferred embodiment of the invention;

FIG. 4 is a table illustrating the various inputs required to provide selective lead switching; and FIG. 5 is an optional circuit which may be utilized to further process the ECG output signal provided by the circuit shown in FIG. 3.

DETAILED DESCRIPTION OF THE INVENTION

The following description is of the best presently contemplated mode of carrying out the invention. This description is not to be taken in a limiting sense but is made merely for the purpose of describing the general principles of the invention. The scope of the invention should be determined with reference to the appended claims.

Figure 1:
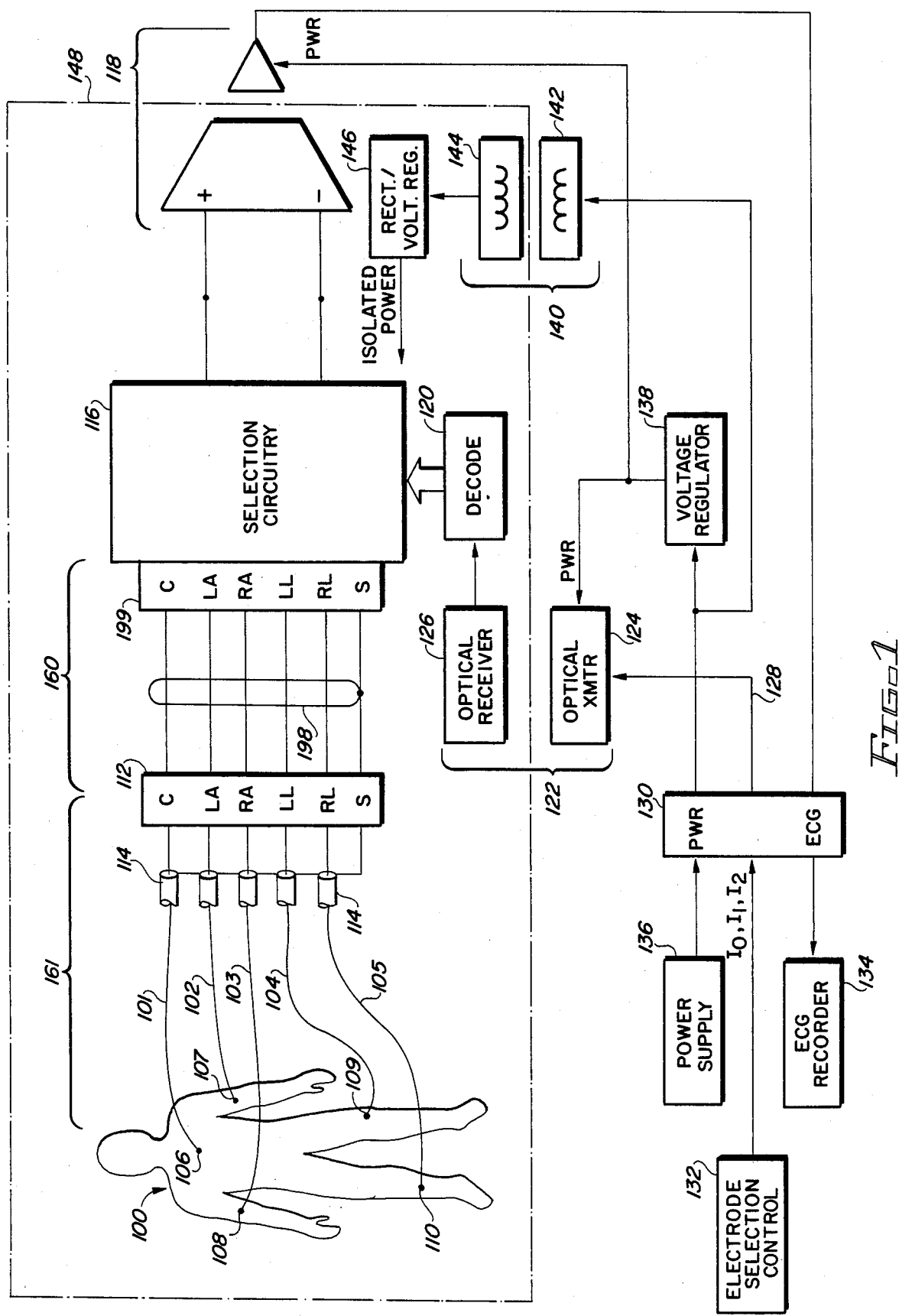
FIG. 1 is a block diagram of the present invention.

A block diagram of the invention is shown in FIG. 1. Leads 101–105, having respective skin electrodes 106–110 at a distal end thereof, provide the interface between a patient 100 and a connector block 112 of a 6-conductor and shield cable 160. In a preferred arrangement, electrode 106 of lead 101 is attached to the chest (C) of the patient 100. Similarly, electrode 107 is attached to the left arm (LA), electrode 108 is attached to the right arm (RA), electrode 109 is attached to the left leg (LL), and electrode 110 is attached to the right leg (RL). Each of the leads 101–105 has a shield 114 therearound, shown only partially in FIG. 1. The various leads 101–105, and the shield 114, comprise a lead assembly 161, with each lead being respectively connected to terminals C, LA, RA, LL, RL, and S of the connector block 112. Note that all of the shields 114 surrounding each lead are electrically tied together and connected to the S terminal of the connector block 112.

Each of the terminals of the connector block 112 are respectively connected to selection circuitry 116 through the cable 160. The function of connector block 112 and lead 160 is simply to provide a convenient means for interfacing the lead assembly 161, comprising the leads 101–105 and electrodes 106–110, to the selection circuitry 116. The selection circuitry 116, in turn, selects desired leads, or combinations of leads, as explained more fully below, for electrical connection with the "+" or "−" input terminals of an isolation amplifier 118. Isolation amplifier 118 functions as a difference amplifier, amplifying the difference between the signals appearing on the "+" and "−" input terminals.

Selection circuitry 116 is controlled by a decode circuit 120. Selection commands are sent to the decode circuit 120 by way of an optical coupler or optical isolator 122. the optical coupler 122 includes an optical transmitter 124 in optical communication with an optical receiver 126. The optical transmitter 124, in turn, is controlled by control signals coupled thereto over three signal line(s) 128. Signal line(s) 128 come, after passing through a designated terminal(s) of a second connector block 130, from electrode selection control circuitry 132. Thus, control signal generated at the electrode selection control circuitry 132 are ultimately used to select the particular patient electrode (or combinations thereof) that are electrically connected to the inputs of the isolation amplifier 118. This is explained in more detail below.

The output of the isolation amplifier 118 is connected to an ECG terminal of the signal connector 130. An appropriate recording or display device 134, such as a conventional ECG chart recorder, is connected to this ECG terminal in order to allow the signal(s) appearing at the output of the isolation amplifier 118 to be recorded or displayed thereon.

A power supply 136 provides the operating power for circuits of the invention. In one embodiment, unregulated power is provided through a power terminal(s) of connector block 130 to a voltage regulator 138. the voltage regulator 138, in turn, provides regulated power to the optical transmitter 124 and an output stage of the isolation amplifier 118. In the preferred embodiment of the invention, the isolation amplifier 118 includes therein means for generating an isolated supply voltage that can be used by the input stage of the isolation amplifier 118 as well as by the selection circuitry 116. If such an isolated power supply is not provided as an intregal part of the isolation amplifier 118, then power supply 136 may also provide unregulated power to an isolation transformer 140 having primary winding(s) 142 and secondary winding(s) 144. A rectifier/voltage regulator 146, connected to the secondary winding(s) 144, provides isolated power for the optical receiver 126, the decode circuit 120, the selection circuitry 116, and an input stage of the isolation amplifier 118.

An important feature of the present invention is that all of the elements or components within the dotted line 148 (FIG. 1), including the patient 100, are electrically isolated from the remaining elements or components of the invention. By "electrically isolated" it is meant that the components within the dotted line 148 are not DC coupled, i.e., they "float" with respect to any reference potentials associated with the components outside of the dotted line 148. Such isolation or "floating" advantageously protects the patient and the equipment from any potentially harmful electrical shock or other electrical hazard. Also, such isolation means that if a shock does occur, the resulting current would be very small ($I = V/Z$) inasmuch as the impedance z between an isolated circuit and a non-isolated circuit is very large.

Shown in FIG. 2 is a perspective view of a diagnostic/programming device 150 within which the present invention is housed in accordance with a preferred embodiment of the invention. The device 150 is primarily used to monitor and/or program implanted cardiac pacemakers. An example of such a device is the AFP Programmer Model 286 manufactured by Pacesetter Systems, Inc. of Sylmar, Calif. Because most of the circuitry and features contained within the AFP Programmer are directed to programming and monitoring implanted cardiac pacemakers, including intercardiac ECG signals (or other physiological signals) sensed by subcutaneous electrodes and/or circuits within the implanted pacemaker, such circuitry is not relevant to an understanding of the present invention and will not be described herein. However, in accordance with the teachings of the present invention, it is sometimes desirable to monitor ECG information as sensed through skin electrodes, either as a separate measurement apart from any measurements made through the implanted pacemaker, or as a supplement to the measurements made by implanted pacemaker. Accordingly, the present invention contemplates the inclusion of the elements shown in FIG. 1 within the circuitry of the diagnostic/programming device 150 shown in FIG. 2.

The device 150 of FIG. 2 includes a built-in chart a recorder 152 as well as a CRT display screen 154. Advantageously, the screen 154 is covered with a touch-sensitive membrane, thereby allowing various control signals, ballons, dials, and the like to be selectively displayed on the CRT screen. The operator can effectuate any desired control by simply touching the screen at the displayed location. Such an arrangement allows a large number of controls and adjustments to be built into the device, limited only by the amount of memory contained therein. Alternatively, conventional control hardware, such as switches, buttons, keyboards, thumb wheel devices, and the like could be used to provide the needed operator control. For purposes of this invention, however, only two operator control functions are really required: (1) a selection mechanism for enabling the function of the present invention, and (2) a selective mechanism for selecting which of the various electrodes attached to the patient are to be coupled to the inputs of the isolation amplifier 118.

Still referring to FIG. 2, the cable 160 is plugged into the connector block 199 located on a rear panel of the device 150. As discussed previously, the cable 160 has attached to it the lead assembly 161 which includes the leads 101–105 and respective electrodes 106–110 as shown in FIG. 1. Once the cable 160 is connected to the device, and the electrodes are positioned as desired on the patient, an appropriate control signal is manually generated by the operator, using the touch-sensitive screen which controls the selection circuitry 116 in a way that electrically connects a desired pair or electrodes/loads from the patient to the isolation amplifier 118. This action allows a desired ECG signal, such as the ECG signal sensed at the chest (C) as measured with respect to the right leg (RL), for example, to be displayed on a suitable recording device, such as the built-in chart recorder 152 of the diagnostic/programming device 150.

Figure 3:
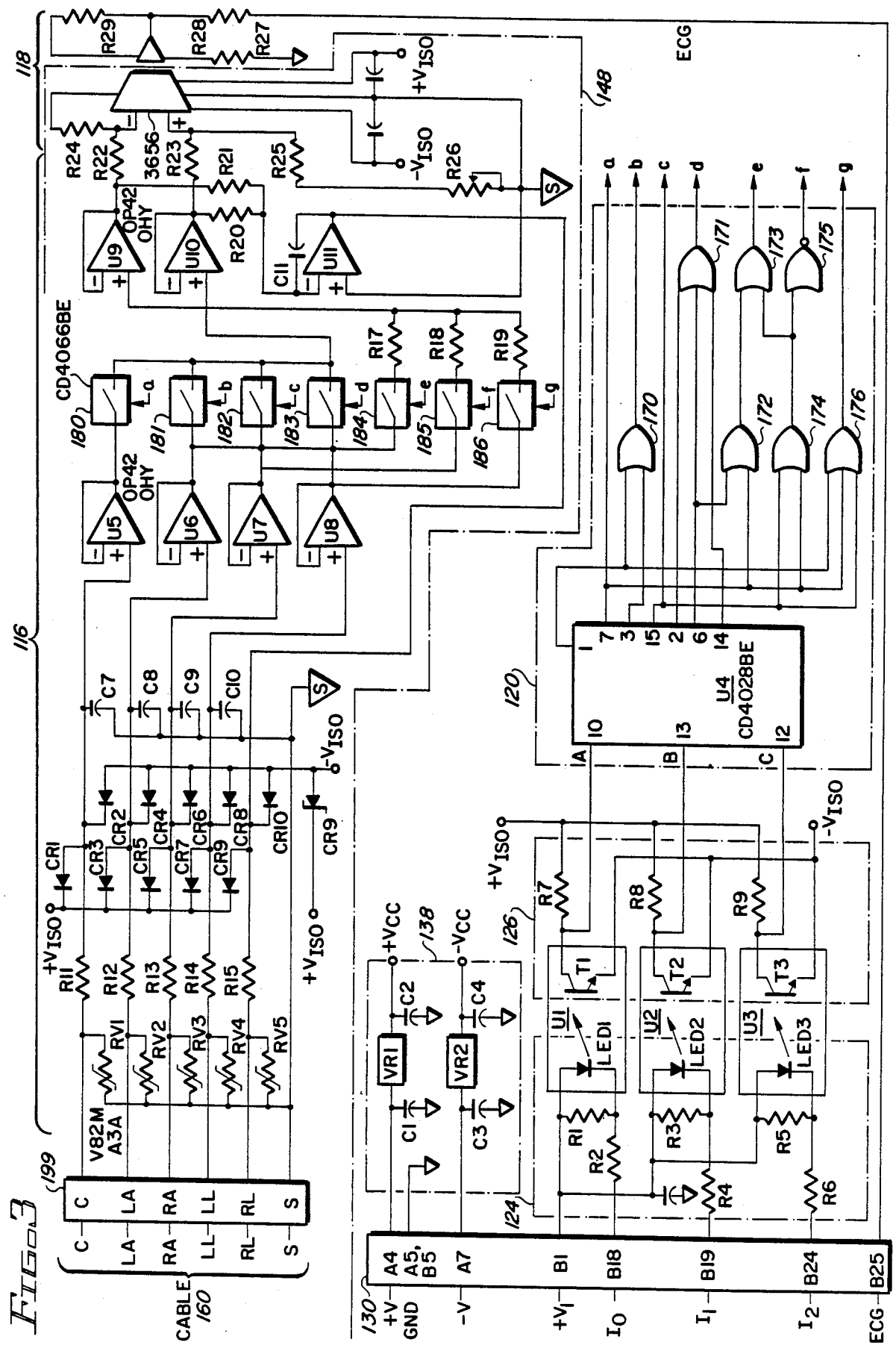
FIG. 3 is a schematic diagram of the circuit of the present invention.

Referring next to FIG. 3, a schematic diagram of the circuit of the present invention is illustrated. The ECG lead/cable assembly 161 as explained above in connection with FIG. 1, includes five conductors from electrodes attached to the patient's chest, left arm, right arm, left leg, and right leg. This lead assembly 161 interfaces with cable 160 at connector block 112. A connector at the other end of the cable 160 is attached to the selection circuitry 116 of the present invention at connector block 199, the connections being labelled C, LA, RA, LL, RL, abd S respectively. The conductors in cable 160 have an electrical shield 198 which is attached to pin S of connector block 112 as indicated in FIG. 3. The leads 101–106 in cable assembly 161 are each individually shielded with shields 114 that are connected to pin S of connector block 112. By means of electrical switching mechanisms depicted in FIG. 3, and described more fully below, an output to a recording device 134 (FIG. 1), for recording the electrical activity sensed at the skin of the patient, is provided at pin B25 of connector 130, with a signal ground reference being provided at pin B6.

The circuit shown in FIG. 3 allows the operator to select different groupings or combinations of the electrical signals obtained from the patient electrodes 106–110 (FIG. 1) for application to the input terminals of amplifier 118, the output of which provides a signal for the ECG recording device. For example, the operator may choose as the output produced for the ECG recording device a signal that is proportional to the difference between a signal obtained from the chest (C) electrode and a signal that represents the average of the three signals obtained from the left arm (LA), the right arm (RA), and the left leg (LL) electrodes. The selections available are standardized in accordance with an established practice in the field. For example, if five electrodes are used (as per the embodiment disclosed herein) a total of seven different combinations can be selected. The present invention allows the operator to select among such combinations by means of control signals $I_0$, $I_1$, and $I_2$ applied through pins B18, B19 and B20, respectively, of connector 130. The control signals which the operator selects to be applied to connector 130 are generated by an electrode selection control device 132 (FIG. 1), which device may be as complex as a microprocessor or as simple as a rotary switch. By selecting the inputs to terminals $I_0$, $I_1$ and $I_2$, the operator can select between eight possible combinations of signals. The control signals may be applied to connector 130 simply by grounding or leaving open connections from $I_0$, $I_1$ and $I_2$ (pins B18, B19, and B20) to the ground reference of the voltage source provided at pins A1 and B1 of connector 130. If pin B18, for example, is grounded, a current will flow through a first light emitting diode (LED1) of optical coupler U1, which current is limited by resistor R2. Similar currents will flow through LED2 or LED3 when pins B19 or B20 are grounded, limited by resistors R4 or R6, respectively. Resistors R1, R2, and R3, in parallel with LED1, LED2 and LED3, respectively, provid a parallel path through which low level currents, such as those generated by noise, will flow. Only when the current reaches a prescribed threshold level will the current flow through LED1, LED2, or LED3. Current flowing through LED1 causes LED1 to emit a light that is sensed by photo transistor T1, which photo transistor is also located within optical coupler U1. The light sensed by transistor T1 causes a current to flow through T1, thereby causing the voltage at terminal A of decoder U4 to drop from approximately $+V_{ISO}$ volts to approximately $-V_{ISO}$ volts. Grounding terminal B19 or B24 of connector 130 causes similar changes in the voltages at pins B and C of decoder U4. Decoder U4, together with the logic and gates 170–176 comprises the decoder circuit 120 shown in FIG. 1. This circuit operates to decode the inputs at the terminals A, B and C of U4 into output voltages of plus or minus $V_{ISO}$ volts at each of the pins labelled a through g of the decoder 120.

The relationship between the input control signals applied at $I_0$, $I_1$ and $I_2$ of connector 130 and the output control signals appearing at a, b, c, d, e, f, and g of the decoder 120, are depicted in FIG. 4. To illustrate, if $I_1$ and $I_2$ are grounded and $I_0$ is left open, thus representing the binary control signal 110 (decimal 6) the terminals a, e, f and g are activated, meaning there is a voltage of $+V_{ISO}$ volts present on these terminals, while the terminals b, c, and d are not activated, meaning there is a voltage of $-V_{ISO}$ present at these terminals. It should be noted that the lead designations I, II, III . . . IV shown in FIG. 4 represent the nomenclature conventionally utilized in the ECG field for the various combinations indicated.

As shown in FIG. 3, the decoder outputs a through g are also connected to semiconductor switches 180–186. These semiconductor switches select the outputs from operational amplifiers U5, U6, U7, or U8, used as buffer amplifiers for the signals received from the C, LA, RA, and LL electrodes, and couple the selected outputs to two operational amplifiers denoted as U9 and U10. The outputs from amplifier U9 and U10, in turn, are applied to the isolation amplifier 118, which isolation amplifier is connected to function as a difference amplifier with a gain typically of 25. An example of an isolation amplifier which may be used to realize the isolation amplifier 118 is isolation Amplifier BB3656 manufactured by the Burr-Brown Corporation of Tuscon, Ariz. This device is interally designed to have isolation between the input and output.

In operation, and by way of further example, assume a setting "V" (FIG. 4) is selected. From the schematic circuit diagram of FIG. 3 and the table of FIG. 4, it is seen that under such conditions the semiconductor switch 180 operates to connect the electrical output from the chest electrode to the "+" input of isolation amplifier 118. At the same time, semiconductor switches 184, 185, and 186 operate to allow amplifier U9 to sum together and divide by three (i.e., to average) the electrical outputs from the right arm, left arm, and left leg electrodes. This averaged signal is then applied to the "−" input of isolation amplifier 118.

Amplifiers U5–U8, connected as unity gain followers, act as buffers or impedance converters between the skin impedance as seen at the skin electrodes 106–110 (FIG. 1) and the input impedance presented by the averaging circuitry of R17, R18 and R19 in combination with U9. That is, amplifiers U5–U8 provide very high input impedance to match the high input impedance typically present at the skin electrodes 106–110. This high input impedance helps assure a high common mode rejection whenever a large electrode resistance difference exists between the various skin electrodes.

As depicted in FIGS. 3 and 4, other combinations of inputs at $I_0$, $I_1$ and $I_2$ as selected by the device operator cause various other combinations of the inputs from the patient to be combined and connected to isolation amplifier 118. As noted in FIG. 3, the right leg electrode 110 of the patient serves as a reference point for the other patient leads. In particular, amplifier U11 averages and filters the signals from amplifiers U9 and U10 and applies this averaged signal to the right leg electrode through resistor R15. In the industry this connection is known as a "driven right leg."

An important feature of the present invention, as mentioned previously, is that through the use of only three electrical isolation devices (optical couplers U1, U2, and U3), and only one output isolation amplifier 118, a high degree of isolation between the grounded portion of the device (the circuitry outside of the dotted line 148 of FIG. 1) and the entire signal selection circuit end front and amplification (the circuitry within the dotted line 148 of FIG. 1) is obtained. The critical isolation points are the three optical couplers and the isolation amplifier 118.

As stated previously, the preferred embodiment of the isolation amplifier 118 is realized using the Burr-Brown Model BB3656 isolation amplifier. This amplifier advantageously includes a floating power supply of plus and minus 8 volts, which floating supply may be used to power the circuitry within the dashed line 148 of FIG. 1. Hence, if this Burr-Brown amplifier or equivalent is used, the isolation transformer 140, and rectifier/voltage regulator 146 shown in FIG. 1 need not be used.

In some circumstances, at the same time that the circuitry of the present invention is attached by means of leads to the patient's chest, arms, and legs, it may be necessary, for medical reasons, to apply a high voltage to the patient's body in an attempt to correct a malfunctioning heart. (An attempt to restore the rhythm of a malfunctioning heart in this manner is called defibrillation.) if unprotected from the high voltages applied to the patient in such circumstances, the circuit of the present invention and ECG recording device itself could be seriously harmed. Accordingly, for the purpose of protecting the device from such high voltages, varistors (resistors having a variable resistance that is a function of an applied voltage), denoted RV1–RV5, are connected between the various inputs from the patient and the shield lead as indicated in FIG. 3. In addition, diodes CR1–CR8 are connected to the various input lines and are biased at either plus or minus $V_{ISO}$. In combination with resistors R11–R14, these diodes serve to limit the excursions of the input voltage to the range of plus or minus $V_{ISO}$ volts. This range adequately protects amplifiers U5, U6, U7 and U8 from damage should a high input voltage be applied. Zener diode CR9 protects against overdriving the plus $V_{ISO}$ voltage line and the minus $V_{ISO}$ voltage line below minus $V_{ISO}$ volts.

If a defibrillator device applies a higher voltage between power line ground and one or all of the electrodes, none of the varistors RV1, RV2, RV3, and RV4, nor diodes CR1–CR8 will open as the entire floating front end will float to whatever high voltage pulse the defibrillator delivers. These varistors and diodes will be useful only if the defibrillator applies a high voltage between any two of the electrodes.

Capacitors C7–C10 (FIG. 3) act as bypass capacitors for frequencies higher than those of interest. Amplifiers U9 and U10 operate as output buffers to sum the output of switches 180–186.

It should be noted that the cable 160 used with the electrodes 106–110 may have limiting resistors (2–10 Kohms) in series with each of the five loads 101–105, for example, at the patient's end of the cable, in order to improve the clamping effect of varistors VR1–VR4.

For some purposes, it may be desirable to connect the ECG output (pin B25 of connector 130 in FIG. 3) to the additional processing circuitry shown in FIG. 5 before providing this output to the ECG recorder. In such circumstances, capacitor C20 provides DC isolation for the amplifiers offset voltage and switch 21 allows the voltage on capacitor C20 to be reset to zero, thereby allowing a simple reset of the baseline (or zero signal) output to the recorder. Typically, C20 and resistor R31 are selected for a 0.05 Hz frequency response. Amplifier 22 provides a selectable gain amplifier to further amplify the ECG signal. Low pass filter 23 allows high frequency components to be filtered from the ECG signal. Preferably, this filter has selectable cut-off frequencies in the range of 35 to 100 Hz, the filter preferably including a switchable IN or OUT notch filter at 60 Hz (power line frequency). As described, the additional processing circuitry of FIG. 5 provides an alternative signal processing circuit that may be used with some recording devices in order to improve the quality of the ECG recording that is made.

The present invention thus provides a simplified circuit used in conjunction with ECG devices, the circuit providing for common mode rejection and a high isolation factor. The circuit utilizes fewer components (one isolation amplifier and three optal isolators or couplers) than conventional ECG devices (one transformer and one operational amplifier for each patient lead), thus making the circuit of the present invention more cost effective. In addition, because the optical isolators are typically fabricated on a single semiconductor chip, thereby allowing them to be housed in a small package, the overall circuit size can be made very small relative to the volume required to package circuits using transformer isolators.

Voltage regulator 138 (FIG. 1 and FIG. 3) includes positive and negative regulators VR1 and VR2 (FIG. 3) that provide a regulated $+V_{cc}$ volt and $-V_{cc}$ power output. These regulators are utilized to drive the output section of isolation amplifier 118, as well as other circuit components outside of the dashed line 148 (FIG. 1). They may be realized using an LM78L12 and an LM79L12, commercially available voltage regulator devices manufactured by National Semiconductor, Inc., of Santa Clara, Calif.

While the invention has been described with reference to a preferred embodiment thereof, it should be understood by those skilled in the art that various changes may be made and equivalence may be substituted for elements described herein without departing from the true spirit and scope of the invention. In addition, many modifications may be made to adapt to a particular situation or circumstance without departing from the essential teachings of the invention. For example, more than five electrode inputs can be provided, one example being 12 electrode inputs. All that would be required for more electrodes would be the use of more buffer amplifiers and switches, and the addition of one or more opto-isolators.

What is claimed is:

1. An electrode selection and isolation apparatus for use with an ECG recording device and at least three electrodes connected to a patient, each of said at least three electrodes including means for sensing an ECG analog electrical signal caused by the contraction of the patient's heart muscle, said electrode selection and isolation apparatus comprising:

isolation amplifier means having first and second input terminals, an output terminal and a reference potential, said first and second input terminals being electrically isolated from said output terminal and reference potential, for generating an electrically isolated output signal at the output terminal as measured with respect to the reference potential, that is derived from an input signal applied between the first and second input terminals;

selection means for electrically coupling a selected one of said at least three electrodes to the first input terminal of said isolation amplifier, and for coupling a selected combination of at least two of the remaining at least three electrodes to the second input terminal of said isolation amplifier, in response to a control signal;

external means for generating said control signal;

optical isolation means for optically coupling said control signal generated by said external control signal generating means to said selection means in a way that electrically isolates the external control signal generating means from said selection means; and means for connecting the output terminal and said reference potential of said isolation amplifier to said ECG recording device;

whereby the ECG recording device and external control signal generating means are completely electrically isolated from the at least three electrodes and the selection means; and further whereby a selected combination of said at least three electrodes can be selectively coupled to said ECG recording device by generating an appropriate control signal at said external control signal generating means.

2. The electrode selection and isolation apparatus of claim 1 further including:

a power supply for providing electrical power to said electrode selection and isolation apparatus, and power supply isolation means responsive to the electrical power provided by said power supply for providing isolated electrical power to the selection means and optical isolation means, said isolated power being electrically isolated from other electrical power used within said electrode selection and isolation apparatus.

3. The electrode selection and isolation apparatus of claim 2 wherein said power supply isolation means is located in said isolation amplifier means.

4. The electrode selection and isolation apparatus of claim 1 wherein said optical isolation means comprises:

an optical transmitter for sending optical signals generated in response to an external control signal generated by said external control signal generating means; and an optical receiver for generating an optically isolated control signal in response to the receipt of said optical signals, said optically isolated control signal being applied to said selection means.

5. The electrode selection and isolation apparatus of claim 4 wherein said external control signal comprises a digital signal, the respective bits of which determine which combination of electrodes are to be selected by the selection means for connection to the first and second input terminals of said isolation amplifier means, and wherein said electrode selection and isolation apparatus further includes decoding circuitry for decoding the bits of the optically isolated control signal and generating appropriate selection signals in response thereto; said selection signals being directed to respective switches located within said selection circuitry.

6. The electrode selection and isolation apparatus of claim 1 wherein said selection means includes protection means for protecting the same from damage if a high voltage is applied to any of said plurality of electrodes.

* * * * *